United States Patent
Glozman et al.

(10) Patent No.: US 12,042,235 B2
(45) Date of Patent: Jul. 23, 2024

(54) GRIPPER FOR ROBOTIC IMAGE GUIDED NEEDLE INSERTION

(71) Applicant: TECHNION RESEARCH & DEVELOPMENT FOUNDATION LTD., Haifa (IL)

(72) Inventors: Daniel Glozman, Kfar Adummim (IL); Gonen Daskal, Kefar Hanassi (IL); Moshe Shoham, Hoshaya (IL); Michael Arad, Tel Aviv (IL); Yoav Pinsky, Beit Keshet (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 0 days.

(21) Appl. No.: 18/195,464

(22) Filed: May 10, 2023

(65) Prior Publication Data
US 2023/0277258 A1    Sep. 7, 2023

Related U.S. Application Data

(63) Continuation of application No. 16/840,579, filed on Apr. 6, 2020, now Pat. No. 11,684,435, which is a
(Continued)

(51) Int. Cl.
*A61B 34/30*    (2016.01)
*A61B 17/34*    (2006.01)
(Continued)

(52) U.S. Cl.
CPC .......... *A61B 34/30* (2016.02); *A61B 17/3403* (2013.01); *A61B 34/20* (2016.02);
(Continued)

(58) Field of Classification Search
CPC ..... A61B 34/32; A61B 34/30; A61B 17/3403; A61B 2034/305; A61B 34/20;
(Continued)

(56) References Cited

U.S. PATENT DOCUMENTS

| 4,765,334 A | 8/1988 | Weiss |
| 6,325,808 B1 | 12/2001 | Bernard et al. |

(Continued)

FOREIGN PATENT DOCUMENTS

| WO | 2007141784 A2 | 12/2007 |
| WO | 2015052719 A1 | 4/2015 |

OTHER PUBLICATIONS

Bogert et al (2005) Respiratory motion compensation with tracked internal and external sensors during CT-guided procedures. Comput Aided Surg. May 2006;11(3):119-25. doi: 10.3109/10929080600740871. PMID: 16829505; PMCID: PMC2386886.
(Continued)

*Primary Examiner* — Diane D Yabut
*Assistant Examiner* — Christina C Lauer
(74) *Attorney, Agent, or Firm* — The Roy Gross Law Firm, LLC

(57) ABSTRACT

A system and method for ensuring safe and tolerable insertion of a needle into a subject's body according to a preplanned or continuously monitored sequence of insertion steps. The system comprises a gripping device for gripping the needle in order to perform robotic insertion steps, yet for releasing the grip between such insertion steps, until the next insertion step is initiated. Thereby, the robot has full control of the needle during insertion steps, but does not constrain the needle between insertions, such that movement of the subject can cause neither damage nor discomfort. The gripping and insertion steps may be coordinated to keep in synchronization with the subject's breathing cycles, such
(Continued)

that the insertion steps may be performed in the same segment of each cycle of motion of the subject's chest. The gripper can either fully disconnect from the needle, or can partially disconnect but constrain motion within limits.

17 Claims, 9 Drawing Sheets

Related U.S. Application Data continuation of application No. 15/027,439, filed as application No. PCT/IL2014/050890 on Oct. 7, 2014, now Pat. No. 10,639,107.

(60) Provisional application No. 61/887,634, filed on Oct. 7, 2013.

(51) Int. Cl.
    *A61B 34/20* (2016.01)
    *A61B 17/00* (2006.01)
    *A61B 90/00* (2016.01)
    *A61B 90/11* (2016.01)

(52) U.S. Cl.
    CPC ............... *A61B 2017/00699* (2013.01); *A61B 2017/3409* (2013.01); *A61B 2034/302* (2016.02); *A61B 2034/303* (2016.02); *A61B 90/11* (2016.02); *A61B 2090/3762* (2016.02)

(58) Field of Classification Search
    CPC .. A61B 2017/00699; A61B 2017/3409; A61B 90/11
    See application file for complete search history.

(56) References Cited

U.S. PATENT DOCUMENTS

| | | | |
|---|---|---|---|
| 10,639,107 | B2 | 5/2020 | Glozman et al. |
| 11,684,435 | B2 | 6/2023 | Glozman et al. |
| 2002/0087065 | A1* | 7/2002 | Yanof ............... A61B 34/70 600/410 |
| 2005/0193451 | A1 | 9/2005 | Quistgaard et al. |
| 2007/0049820 | A1 | 3/2007 | Stern et al. |
| 2008/0167663 | A1 | 7/2008 | De Mathelin et al. |
| 2008/0221520 | A1 | 9/2008 | Nagel et al. |
| 2010/0234856 | A1 | 9/2010 | Stoianovici et al. |
| 2011/0295108 | A1* | 12/2011 | Cox ............... A61B 8/4444 600/424 |
| 2012/0083801 | A1 | 4/2012 | Nixon |
| 2012/0190981 | A1* | 7/2012 | Harris ............... A61B 5/14 604/95.01 |
| 2014/0318299 | A1 | 10/2014 | Oyola et al. |

OTHER PUBLICATIONS

Locklin et al. Respiratory biofeedback during CT-guided procedures. J Vasc Interv Radiol. Jun. 2007;18(6):749-55. doi: 10.1016/j.jvir.2007.03.010. PMID: 17538137; PMCID: PMC2562717.

PCT International Search Report for International Application No. PCT/IL2014/050890, mailed Jan. 29, 2015, 3 pp.

PCT Written Opinion for International Application No. PCT/IL2014/050890, mailed Jan. 29, 2015, 6pp.

Supplementary European Search Report for corresponding European Patent Application No. EP 14851843 mailed May 10, 2017, 10pp.

\* cited by examiner

GRIPPER FOR ROBOTIC IMAGE GUIDED NEEDLE INSERTION

CROSS-REFERENCE TO RELATED APPLICATIONS

This application is a continuation of U.S. patent application Ser. No. 16/840,579, filed Apr. 6, 2020, which is a continuation of U.S. patent application Ser. No. 15/027,439, filed Apr. 6, 2016, now U.S. Pat. No. 10,639,107, which is a U.S. National Phase Application under 35 U.S.C. 371 of International Application No. PCT/IL2014/050890, which has an international filing date of Oct. 7, 2014, and which claims the benefit of priority from U.S. Provisional Patent Application No. 61/887,634, filed Oct. 7, 2013, the disclosures of which are incorporated herein by reference in their entirety.

FIELD OF THE INVENTION

The present invention relates to the field of needle holding devices for image guided needle insertion, especially using robotic insertion.

BACKGROUND

Many routine treatments employed in modern clinical practice involve percutaneous insertion of needles and catheters, such as for biopsy or drug delivery. The aim of a needle insertion procedure is to place the tip of an appropriate needle safely and accurately in a lesion, organ or vessel. Examples of treatments requiring needle insertions include vaccinations, blood/fluid sampling, regional anesthesia, tissue biopsy, catheter insertion, cryogenic ablation, electrolytic ablation, brachytherapy, neurosurgery, deep brain stimulation and various minimally invasive surgeries.

There is a growing trend of performing needle insertion with offline or intra-operative image guidance. Guiding the needle based on offline images has a disadvantage, because the patient keeps breathing and the offline image then becomes historic in nature. In addition, because of gravitational force the abdomen soft tissues deform with time. The imaging scan is thus valid for several seconds only.

Even when the needle is inserted under real-time, fluoroscopic vision of the needle insertion procedure is not simple and requires proficient performance. Moreover as shown in the PCT published application WO 2007/141784 for "Controlled Steering of a Flexible Needle", having a common co-inventor with the present application, the needle can be inserted in numerous ways even when the needle tip is required to follow the same trajectory.

In order to overcome these difficulties and improve needle placement accuracy, use is made of the model for flexible needle steering and control in soft tissue, as described in the above referenced PCT. As shown there, the manipulation required on the needle base is too complex to perform manually. Therefore the needle insertion is performed with a robot.

In a typical robotic image guided needle insertion procedure, the needle insertion will be done step-wise. The needle is not inserted in a single iteration for safety reasons. The usual procedure flow is as follows:
1. An image is taken with the needle and the target.
2. The operator analyses the image and decides whether correction to the movement is necessary.
3. The robot is then commanded to move the needle by the next step.

It can take from several seconds to several minutes to take the image and to decide how to proceed. During this time the patient continues breathing with the needle inside his/her body, such that its position is constantly changing, albeit quasi-periodically. Even when the procedure is performed without operator feedback, being based only on image data, besides the quasi-periodic breathing motion, the patient may also move his body because of pain or a cough. If the needle base is held stiffly by the insertion robot, a fixed needle could cause injury, or at least discomfort or pain to the patient.

There therefore exists a need for an automatic needle insertion system which reduces or eliminates the danger of the insertion procedure, and reduces discomfort to the subject.

The disclosures of each of the publications mentioned in this section and in other sections of the specification, are hereby incorporated by reference, each in its entirety.

SUMMARY

The current disclosure describes a novel system and method for ensuring the safe and tolerable insertion of a needle into a subject's body according to a preplanned or a continuously monitored sequence of insertion steps. The system comprises a device for gripping the needle in order to perform robotic insertion steps, yet for disconnecting rigid mechanical contact with the needle between such insertion steps, until the next insertion step is initiated. By this means, the robot has full control of the needle during each insertion step, but does not constrain the needle at all between insertion steps, such that movement of the subject should cause neither damage nor discomfort. The gripping actions and insertion steps may advantageously be coordinated by the combined robot/gripper control system to keep in synchronization with the subject's breathing cycles, such that the insertion steps are generally performed in the same part of each cycle of motion of the subject's chest and any organs which move with it. Assuming that the time for each insertion step is significantly shorter than the subject's breathing cycle time, this arrangement also has the advantage that the robot can take up its grip on the needle at approximately the same position on the needle as the position at which it released the grip, either one or several breathing cycles previously.

The methods include either full disconnection, where the disconnected needle is free to move in space between insertion steps, or partial disconnection, which leaves a partial limiting linkage with the gripper, allowing the needle free movement with one or more limited degrees of freedom. The connecting mechanism can employ magnetic, electrostatic or other attraction forces or it can incorporate a mechanical connector. It should be such as to operate within a time which is only a small fraction of the breathing cycle time, so as to minimize any interference of the breathing motion with the insertion step.

The gripper must be able to grip the needle firmly, such that the force required to insert the needle into the subject can be transferred to the needle. For this reason, it is generally impractical to grip the needle directly, because of the thin diameter of most needles, and the needle is generally held in a needle holder accordingly designed. The needle holder is then adapted to be gripped or released by the gripper, and may also incorporate sensing elements to enable determination of its position relative to the gripper. It may also be feasible to use a needle with a thickened shaft section where the gripping is performed, and it should be understood that this invention is not intended to be limited by the physical nature of the way in which the needle itself is gripped. In co-pending PCT Application, filed by the same applicant as the present application, and claiming priority from U.S. Provisional Patent Application 61/887,634, for "Needle Steering by Shaft Manipulation", there is described a dedicated robotic system and needle gripper for gripping and inserting a needle into a patient, and this needle gripper could also be used as the functional element of the present application. When reference is made to gripping of the needle hereinbelow, it is to be understood that the meaning is either to gripping of the needle itself or more usually, to gripping of the needle holder. Likewise, the needle location may mean either the needle location itself or the needle holder location, depending on context.

The device can also include an optical, magnetic, ultrasound or other tracking device, which tracks the needle's or the needle holder's location in space relative to that of the gripper, whose position is known from the robot's control system. When connection is required, the robot moves the gripper close to the needle position using the tracking information and then catches the needle or its holder using its capture mechanism.

The needle movement may be quasi-periodic because of the patient's breathing or sporadic movements, such as from a cough or because of pain. Because the exact needle position in space is unpredicted in such cases, it will generally be difficult to bring the robot exactly to the needle in order to catch it. Therefore the catching device should have the ability to grip the needle even if the gripper does not perfectly coincide with the needle. In such a case, the connection to the needle should preferably be done in the same region in space where the needle was left the previous time, which, at least because of the breath synchronization process, will approximately correspond to the same stage in the breath cycle. The robot will come to the point where it previously left the needle and will wait for the needle there. It is possible to use the tracking device which tracks the needle movement to also track the patient's breathing motions. Additionally, for ventilated patients, it is possible to use a signal from the ventilator in order to determine the predetermined gripping point in the patient's breath cycle, and to synchronize therewith.

There is thus provided in accordance with an exemplary implementation of the devices described in this disclosure, a system for needle insertion into a subject, the system comprising:
  (i) a capture unit comprising a mechanism for alternately gripping and releasing either of the needle or a holder incorporating the needle, and
  (ii) a controllable drive mechanism adapted to insert the needle into the subject in a series of separate steps,
wherein the controllable drive mechanism is synchronized with the capture unit mechanism such that the capture unit grips the holder during an insertion step, and releases the holder between insertion steps.

Such a system may further comprise a tracking system for determining the position of the needle or the holder relative to the capture unit. The tracking system may comprise sets of emitters and sensors, wherein one of the set of emitters and the set of sensors may be disposed on the needle or the holder, and the other one of the set of emitters and the set of sensors may be disposed on the capture unit.

In any of the above described systems, the controllable drive mechanism may be adapted to synchronize the insertion steps with the breathing cycle of the subject, such that the capture unit can be commanded to grip the needle or the holder at a predetermined point in time of the subject's breathing cycle. For such a case, the system may further comprise at least one tracking sensor to monitor the subject's breathing cycle. The tracking sensor then determines the position of the body of the subject close to the point of insertion of the needle. Furthermore, the at least one tracking sensor may be part of an external tracking system, or part of a sensing system operative between the body of the subject close to the point of insertion of the needle and at least one of the controllable drive mechanism and the capture unit.

In these implementations, the predetermined point in time of the subject's breathing cycle may be obtained from a signal derived from a ventilator. Furthermore, the capture unit may be commanded to grip the needle or the holder at the same general point in time of the subject's breathing cycle as a previous release point of time of the holder in the breathing cycle. If so, then the robotically guided capture unit may anticipate the position of the needle or the holder between subsequent insertion steps, from the position of release of the needle or the holder following a previous insertion step.

In any of the above described systems, the controllable drive mechanism may be either a robotic actuator attached to the capture unit, or a motion mechanism adapted to move the needle or the holder relative to the capture unit.

Additionally, alternative implementations of any of the above-described systems may further involve a system for needle insertion into a subject, the system comprising:
  (i) a needle holder for holding the needle, the holder having a protrusion,
  (ii) a gripper device having mechanical clamping jaws, and
  (iii) an actuating mechanism adapted to close the clamping jaws on the protrusion, such that the needle holder is clamped by the gripper device,
wherein the gripper device is adapted to be held by a robot, such that when the actuating mechanism is operated, the robot can insert the needle into the subject.

In such an implementation, the protrusion may have a generally cylindrical shape, and the mechanical clamping jaws may form a peripheral barrier to the needle holder, to confine movement of the needle holder therewithin when the needle holder is not clamped by the gripper device. Either of the above implementations may further comprise sets of emitters and sensors, wherein one of the set of emitters and the set of sensors is disposed on the needle holder, and the other one of the set of emitters and the set of sensors is disposed on the gripper device, such that the position of the needle holder relative to the gripper device can be determined. The system may then further comprise an external tracking system for determining the positions of the needle holder and the gripper device, such that the position of the needle holder relative to the gripper device can be determined.

Another example implementation provides a system for needle insertion into a subject, the system comprising:
  (i) a needle holder for holding the needle, the holder having a base with a first set of locating features, and a locating spigot,
  (ii) a gripper device having a second set of locating features, adapted to mate with the first set of locating features on the needle holder, and a clamping system adapted to close on the spigot, and
  (iii) an actuating mechanism adapted to close the clamping system on the spigot, after the first and second locating features are mated, such that the needle holder is clamped by the gripper device, wherein the gripper device is adapted to be held by a robot, such that when the actuating mechanism is operated, the robot can insert the needle into the subject. The system may then further comprise sets of emitters and sensors, and either one of the set of emitters and the set of sensors may be disposed on the needle holder, and the other one of the set of emitters and the set of sensors disposed on the gripper device, such that the position of the needle holder relative to the gripper device can be determined. Additionally, the system may further comprise an external tracking system for determining the positions of the needle holder and the gripper device, such that the position of the needle holder relative to the gripper device can be determined.

A yet further exemplary implementation of the systems for needle insertion into a subject, described in this disclosure may comprise:
  (i) a needle holder for holding the needle, the holder having a base with a first set of locating features and a ferromagnetic section,
  (ii) a gripper device having a second set of locating features, adapted to mate with the first set of locating features on the needle holder, and a switchable source of magnetic field, and
  (iii) an actuating mechanism adapted to switch the magnetic field on such that the first and second locating features are mated, and the ferromagnetic section of the needle holder is clamped by the magnetic field of the gripper device,
wherein the gripper device is adapted to be held by a robot, such that when the actuating mechanism is operated, the robot can insert the needle into the subject.

Such a system may further comprise sets of emitters and sensors, wherein either one of the set of emitters and the set of sensors is disposed on the needle holder, and the other one of the set of emitters and the set of sensors is disposed on the gripper device, such that the position of the needle holder relative to the gripper device can be determined. The system may also advantageously further comprise an external tracking system for determining the positions of the needle holder and the gripper device, such that the position of the needle holder relative to the gripper device can be determined.

Still other example implementations involve a system for needle insertion into a subject, the system comprising a needle holder for holding the needle, the holder having a flexible cord attached thereto, and a gripper device, the gripper device comprising:
  (i) an actuator to which the flexible cord may be attached remotely from the needle holder, and adapted to draw in the flexible cord when actuated,
  (ii) a docking port shaped such that the needle holder fits firmly therein when the flexible cord is drawn in, and
  (iii) a pair of arms disposed on either side of the docking port, to confine movement of the needle holder therebetween,
wherein the gripper device is adapted to be held by a robot, such that when the actuating mechanism is operated, the needle holder is docked firmly in the docking port, and the robot can insert the needle into the subject.

This system may further comprise sets of emitters and sensors, wherein either one of the set of emitters and the set of sensors is disposed on the needle holder, and the other one of the set of emitters and the set of sensors is disposed on the gripper device, such that the position of the needle holder relative to the gripper device can be determined. Alternatively, the system may further comprise an external tracking system for determining the positions of the needle holder and the gripper device, such that the position of the needle holder relative to the gripper device can be determined.

Another example implementation can involve a method for needle insertion into a subject, the method comprising:
  (i) providing a holder incorporating the needle,
  (ii) providing a capture unit for controllably gripping and releasing the holder, and
  (iii) robotically guiding the capture unit to insert the needle into the subject in a series of separate steps, comprising:
    (a) gripping the holder in the capture unit during an insertion step of the needle, and
    (b) releasing the holder from the capture unit between insertion steps.

In such a method, the insertion steps may be synchronized with the breathing cycle of the subject, such that the capture unit can be instructed to grip the holder at a predetermined point in time of the subject's breathing cycle. This method then may further comprise the step of monitoring the subject's breathing cycle using a tracking sensor, or may further comprise the step of monitoring the subject's breathing cycle using a signal obtained from a ventilator. The tracking sensor may determine the position of the body of the subject close to the point of insertion of the needle. Alternatively, the method may further comprise the step of instructing the capture unit to grip the holder at the same general point in time of the subject's breathing cycle as a previous release point of time of the holder in the breathing cycle. Finally, in any of these methods, the robotically guided capture unit may be configured to anticipate the position of the holder between a subsequent insertion step from the position of release of the holder following the previous insertion step.

BRIEF DESCRIPTION OF THE DRAWINGS

The present invention will be understood and appreciated more fully from the following detailed description, taken in conjunction with the drawings in which:

FIG. 6d also shows schematically an additional implementation in which the gripper is used also in order to advance the insertion of the needle step by step into the patient.

DETAILED DESCRIPTION

There are many methods by which the needle gripping functions described in this disclosure can be performed, and the mechanics of such methods are numerous. Without wishing to limit the generality of the devices and methods described in this disclosure, a number of such mechanisms are now described, merely as non-limiting examples of how the present invention could be practically implemented. The types of needle gripper mechanisms described can be divided into two main groups:
(i) Grippers which fully disconnect from the needle, and
(ii) Grippers in which the needle connection is freed, but the needle base is constrained.

These groups are now described in separate sections hereinbelow.

(i) Fully Disconnecting Grippers

The needle is disconnected fully, and sensors keep track of the needle base location, so that the robot can be positioned in the correct position in order to catch the needle when commanded to do so. A number of possible alternative implementations are possible for achieving this, as follows:
Catching Using a Mechanical Gripper.

Figure 1A:
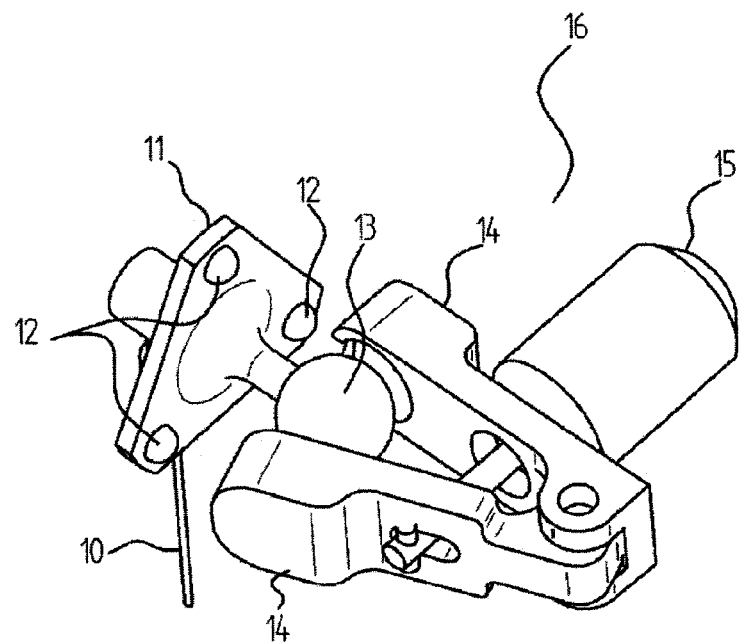
FIGS. 1a, 1b, 1c illustrate schematically a first exemplary gripper using a mechanical clamping implementation.
Figure 1B:
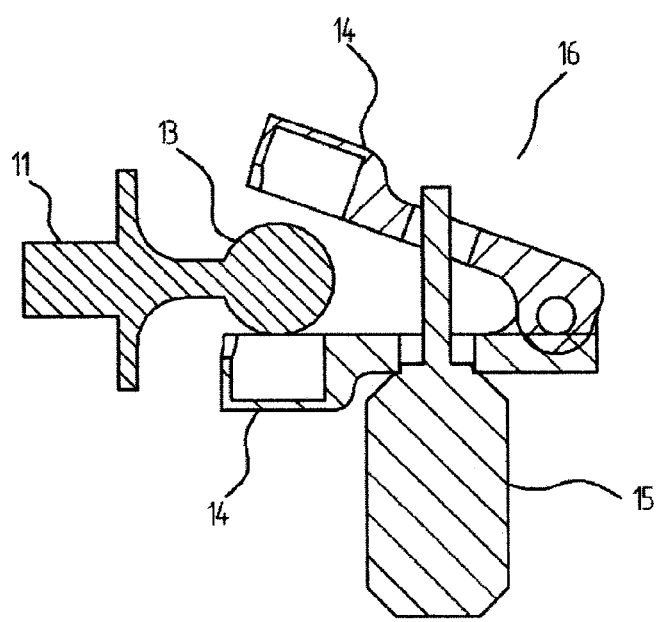
Figure 1C:
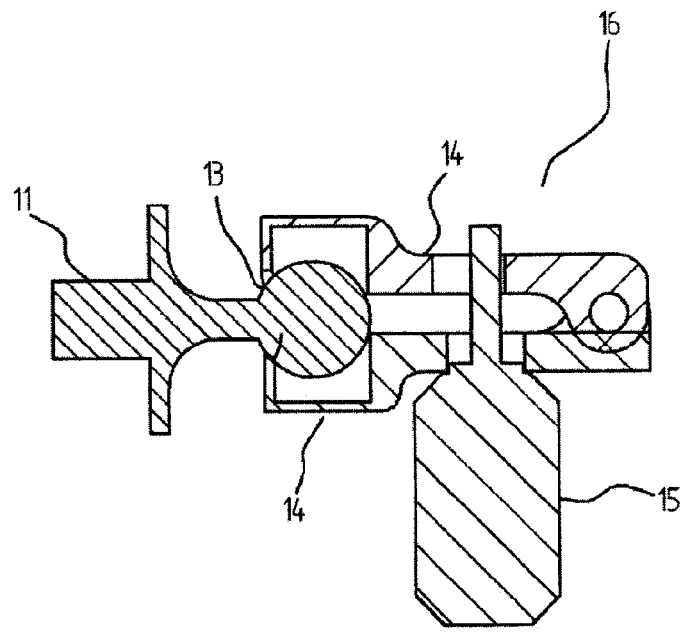

Reference is made to FIGS. 1a, 1b, 1c, which illustrate schematically a first exemplary gripper using a mechanical clamping implementation. FIG. 1a is an isometric view of the griper 16, while FIGS. 1b and 1c are cross sectional views, showing the gripper respectively open and gripped shut on the needle. The needle 10 is connected to a lightweight needle holder 11 which has a clamping element in the form of a ball 13 attached to it. This ball can be clamped by the needle holder gripper 16. This ball is kept located within the slightly opened jaws of a clamp 14, but is only gripped when the jaws are closed by operation of the actuator 15, which can be mechanically, pneumatically or electro-magnetically actuated. Sensors 12 located on the needle holder can track the needle holder position and orientation in real-time. One method of tracking the needle holder position and orientation could be by means of an external tracking system remotely mounted from the needle and robot. A more advantageous method may be to mount the tracking system emitters on the gripping mechanism 16 which is held by the robotic actuator. This will be fully described below in relation to the example grippers of FIGS. 3a-3b. The emitters/sensors for the tracking functions could be ultrasound proximity sensors, infra-red, laser, magnetic, static or any other system which measures distance or relative position between objects. When there is a need to connect to the needle, the robot moves the needle catcher clamps 14 close to the needle holder ball, as shown in FIG. 1b, using the tracker system to ascertain where the ball should be situated, and activates the clamps 14 to grip the needle holder as shown in FIG. 1c.
Disconnecting by Means of a Flexible Link that can be Made Rigid on Demand.

Figure 2:
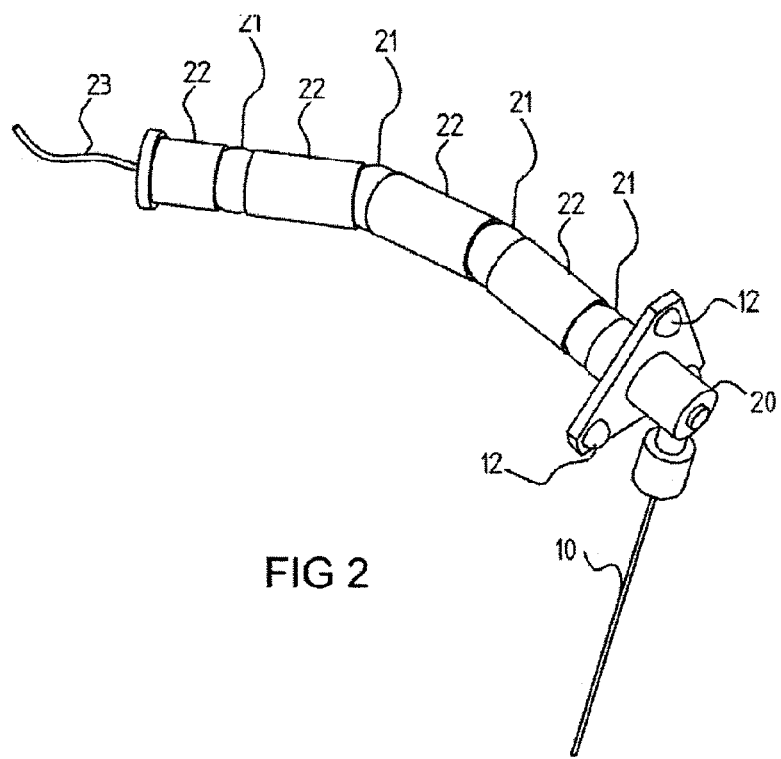
FIG. 2 illustrates schematically a needle holder connected to the robot by a flexible link.

Reference is now made to FIG. 2. The needle holder 20 is always connected to the robot by a flexible link, such as one composed of rigid tubes 22 and spherical ball joints 21, as shown in FIG. 2. The flexible link can be stiffened on demand by pulling the wire 23. Using this connection the needle can instantly be gripped wherever it is located. The orientation of the needle holder relative to the robot is known from the sensors 12.
Catching using a Magnetic Gripper.

Figure 3A:
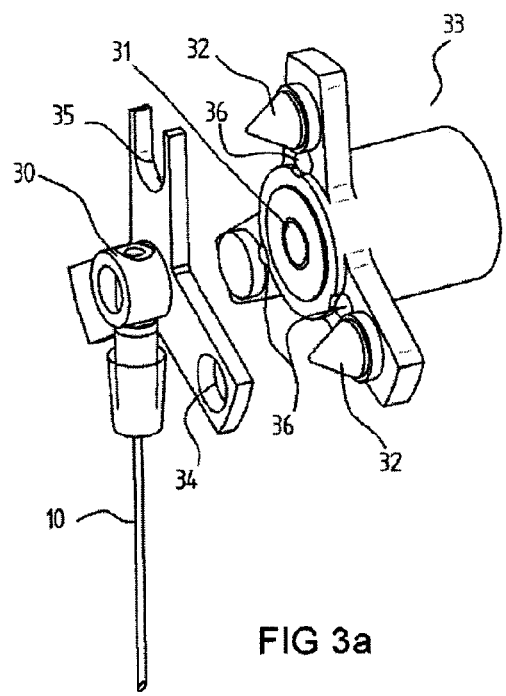
FIGS. 3a and 3b show two views of a magnetic gripper, taken from different isometric angles of view.
Figure 3B:
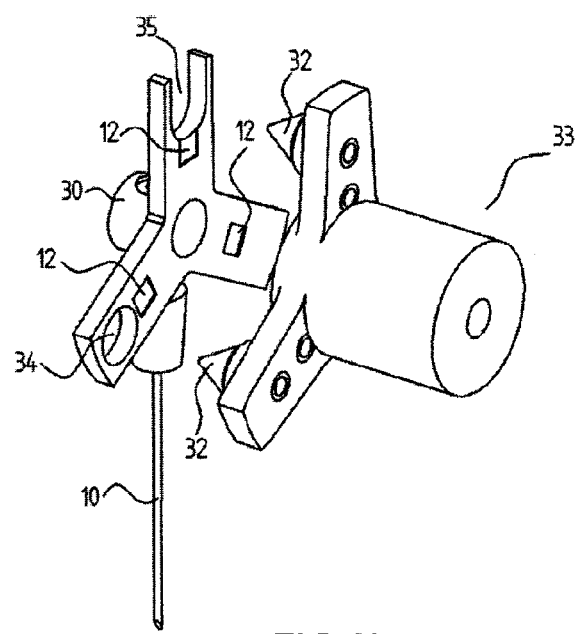

Reference is made to FIGS. 3a and 3b, which show two views of a magnetic gripper, taken from different isometric angles of view. The needle 10 is connected to a lightweight needle holder 30 with a triangular spider-like base in which are disposed at least two locating holes 34 or one locating hole 34 and one locating slot 35. In the example shown in FIGS. 3a, 3b, a hole 34 and slot 35 implementation is shown. The needle catcher 33 has auto-orienting pins 32, which are dimensioned and spaced to mate with the spider base openings 34, 35. The one or more sensors 12 track the needle holder 30 in real-time. The sensors 12 can be ultrasound proximity sensors, infra-red, laser, magnetic, static or other sensor which measures distance or relative position of an object.

A more advantageous method than the use of an external tracking system may be to mount the tracking system emitters 36 on the gripping mechanism 16 which is held by the robotic actuator. The emitters 36 and sensors 12 can then determine the mutual position of the nearby needle holder 11, whose position is then known relative to the capture mechanism 16, or even absolutely in space, since the robot pose can be known absolutely in space. Alternatively, the emitters 36 could be on the needle holder 11 and the sensors on the capture mechanism 16, or the emitters and sensors could incorporated in the same package on one of these two component parts of the system, and their relative sensed position be acquired by means of a reflector on the opposing component.

The needle base is kept connected to the needle catcher by means of magnetic attraction forces of actuator 31, powered by an electromagnet 33, though a solenoid driven moving magnet may also be used. The needle base is kept aligned by means of the aligning pins 32. When there is a need to disconnect from the needle the magnetic force is removed and the needle can disconnect and move freely in space, while the sensors 12 keep track of needle position. When there is a need to connect to the needle, the robot moves the needle catcher close to the needle holder position, so that the orienting pins coincide with the relevant openings in the spider base, and the magnetic force is applied which pulls the spider base into contact with the catcher.
Catching using Mechanical Gripper.

Figure 4A:
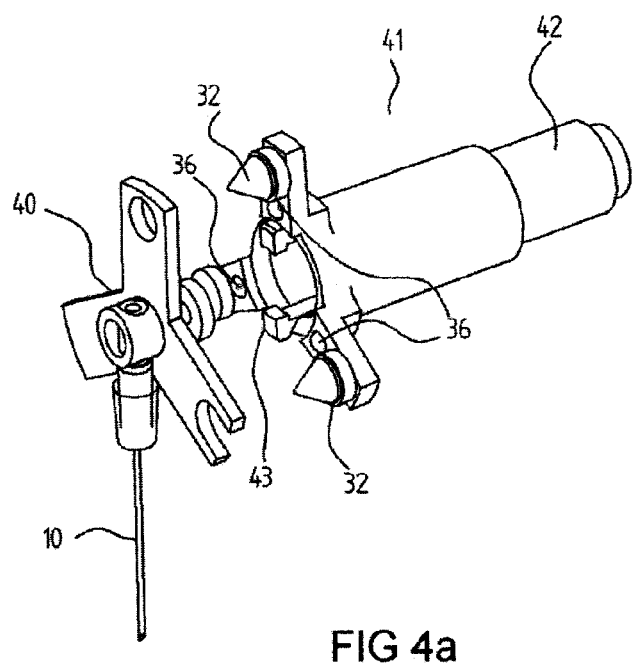
FIGS. 4a to 4d show different views of a needle holder similar in structure to the magnetic gripper implementation shown in FIGS. 3a to 3b, but in which the gripping is done mechanically.
Figure 4B:
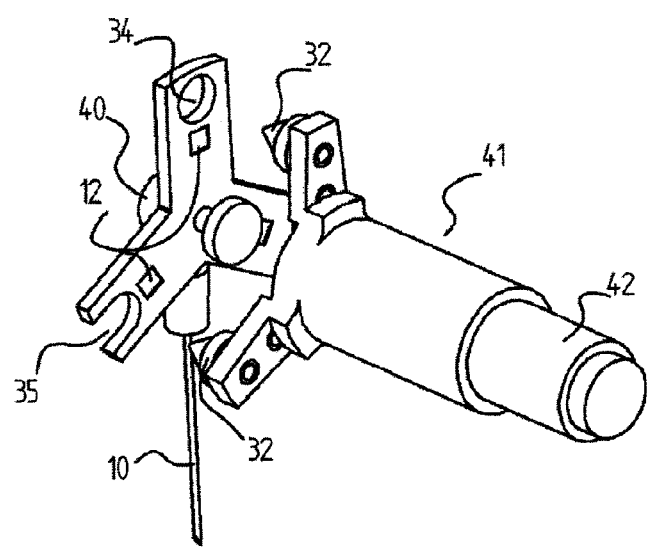
Figure 4C:
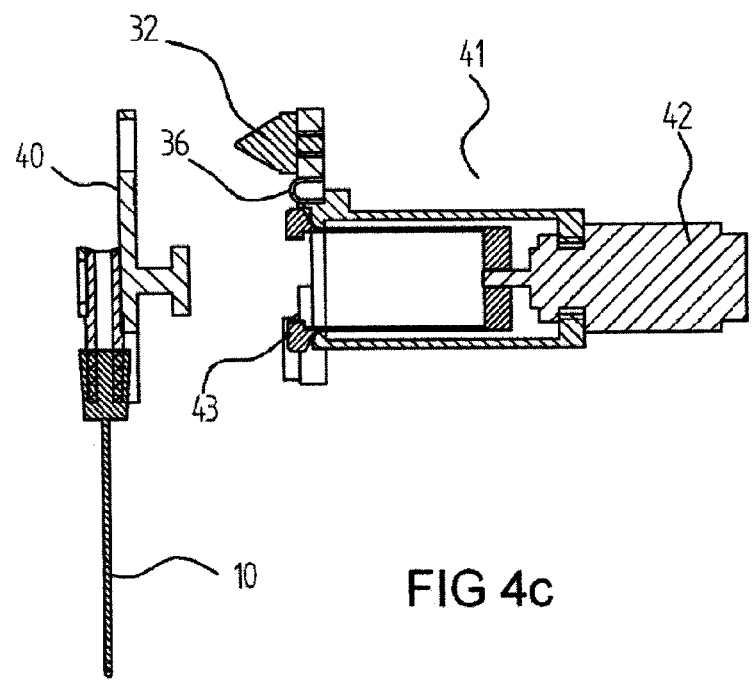
Figure 4D:
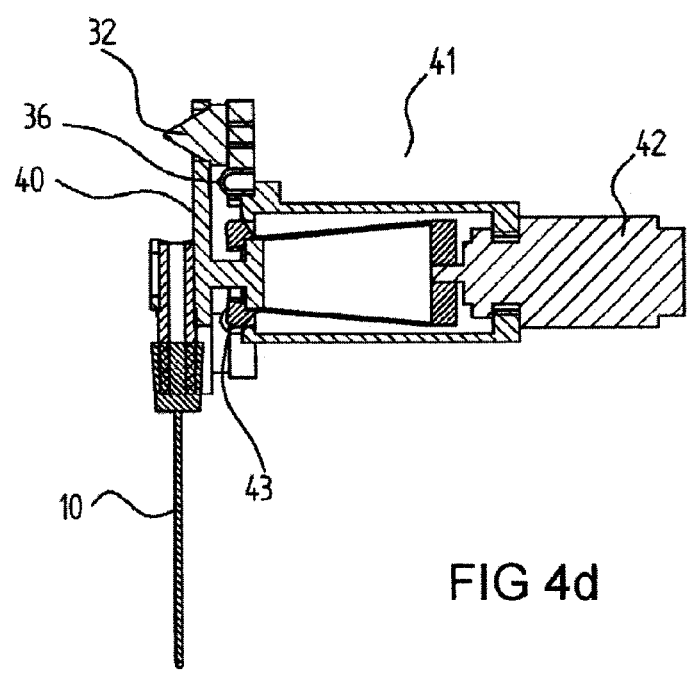

Reference is made to FIGS. 4a to 4d, which show different views of a needle holder similar in structure to the magnetic gripper implementation shown in FIGS. 3a to 3b, but in which, instead of the magnetic clamping of FIGS. 3a to 3b, the gripping is done mechanically with a clamp 43 actuated by a solenoid or motor 42, which tightens onto a post element in the needle holder 40. FIGS. 4a and 4b are overall isometric views of the gripper 41 and needle holder 40, taken from two different directions to show all aspects of the gripping mechanism, while and FIGS. 4c and 4d are cross sectional drawings showing how the mechanical clamping operation takes place.

(ii) Freeing the Needle Connection but Constraining the Needle

Figure 5:
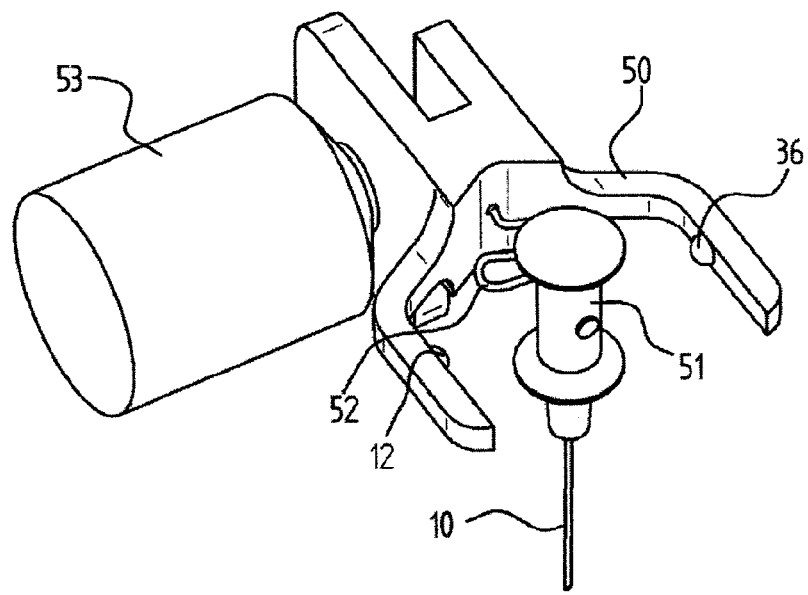
FIG. 5 shows a second type of needle gripper, in which the needle holder is freed from positive contact with the gripper device, but is held within the confines of a defined space outside of which it cannot move.

Reference is now made to FIG. 5, which shows a first example of the second type of needle gripper, in which the needle holder is freed from any positive contact with the gripper device, but is held within the confines of a defined space outside of which it cannot move, such that robotically moving the gripper to the region of the needle holder, and then regripping the needle holder can be done efficiently and speedily. In the example of FIG. 5, the needle holder 51 is gripped in a predefined and repeatable position of the gripper device by means of a tensioned wire 52. When the needle holder is released, it is constrained by a flexible wire 52 and by the static jaws 50 which constrain the needle position to within its confines. The needle position and orientation may be tracked by the sensors 12 and the length of the released wire 52. When re-connection is required, the wire is pulled back into the needle catcher by means of actuator 53.

Figure 6A:
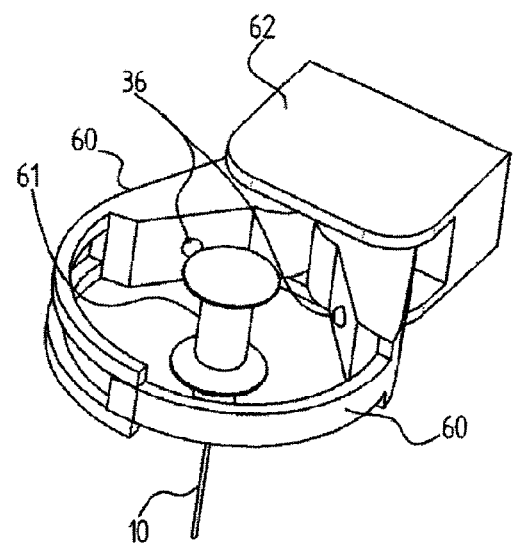
FIGS. 6a, 6b show an additional example of a semi-constrained needle gripper assembly.
Figure 6B:
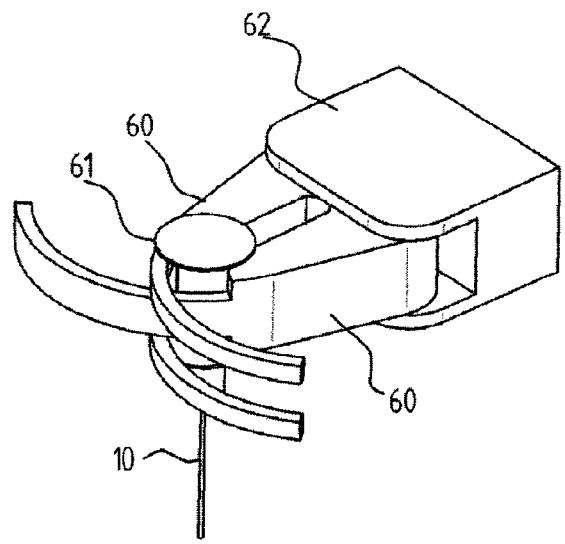

Reference is now made to FIG. 6a, 6b, which show an additional example of a semi-constrained needle gripper assembly. The needle holder 61 is disconnected fully but is constrained by a circle structure created by clamp arms 60. When catching of the needle is required, the catcher 62 is moved by the robot such that the needle base will be located in the center of the circle created by the clamps 60. Then the clamp arms are closed, as shown in FIG. 6b.

Figure 6C:
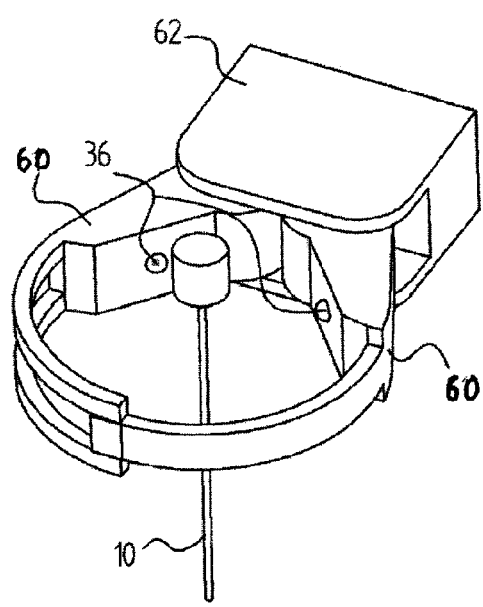
FIGS. 6c and 6d show a similar arrangement to that of FIGS. 6a and 6b, but wherein the needle is clamped directly.
Figure 6D:
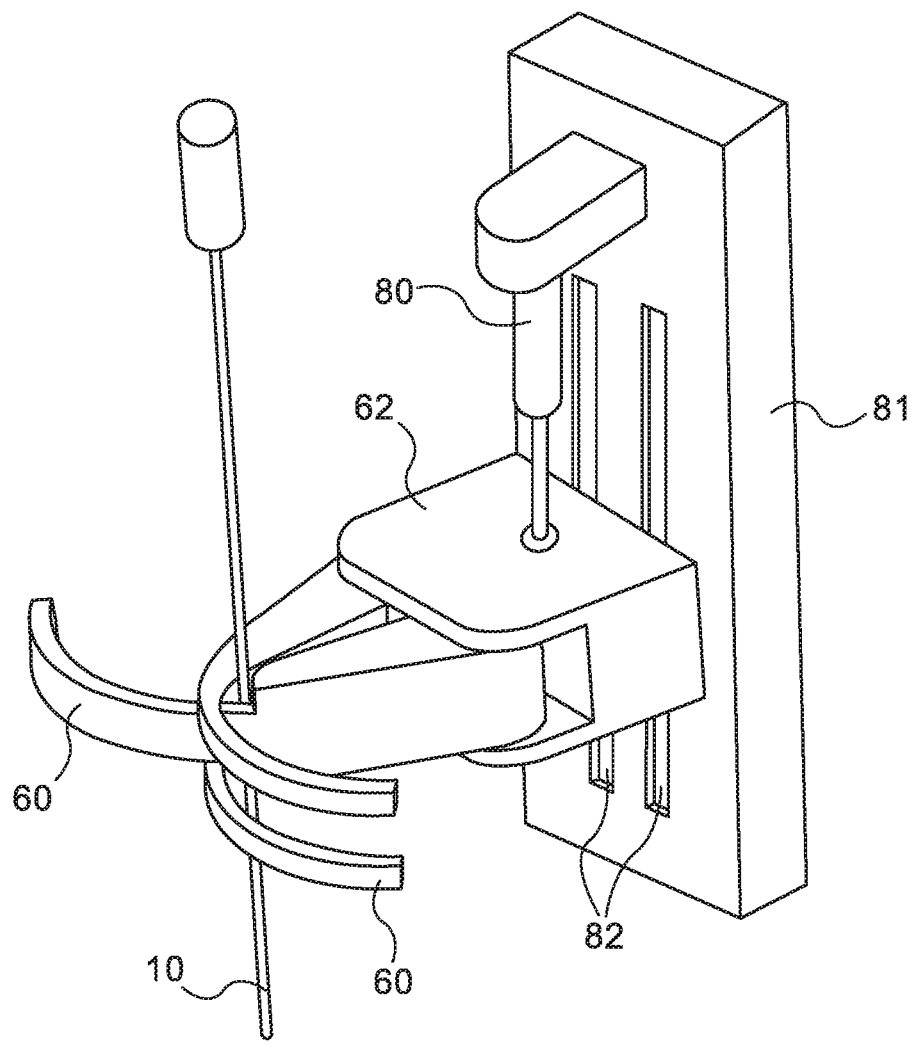

FIGS. 6c and 6d show a similar arrangement but wherein the needle is clamped directly instead of through a shank having an increased diameter for gripping, as in FIGS. 6a and 6b.

FIG. 6d also shows an additional implementation of the needle grippers of the present disclosure, in which the gripper is also used in order to advance the insertion of the needle step by step into the patient. The gripper incorporates an insertion mechanism that enables the gripper itself to advance the needle or the needle holder step by step. This can be used either entirely in place of the robotic insertion, or in addition to the robotic insertion, such as when the robot is used for initial positioning or for large insertion steps, and the insertion mechanism implementation of FIG. 6d is used for small incremental insertion steps. In this exemplary implementation, a motion mechanism is associated with the needle gripper, and is adapted to move the needle distally by a predetermined amount once the gripper has caught the needle or the needle holder firmly in its grip. The motion mechanism can be of any controllable type, and most conveniently may be electro-mechanical, such as using a mechanical slide and a lead screw, or electromagnetic, using a linear solenoid, or hydraulic or pneumatic, using a driven piston. The extent of the motion imparted to the needle gripper is determined by the signal imparted by the control system, according to the step size selected by the medical personnel. In the implementation shown in FIG. 6d, the insertion mechanism is made up of a slide base 81, which may be attached to the end effector of the robotic placement arm, with a set of rails 82, along which the base of the needle gripper 62 can run, under the influence of the motion mechanism, shown in FIG. 6d as a piston 80. The base 81 can preferably be held by the end of the robot effector arm. The motion insertion mechanism of FIG. 6d can be applied to incrementally insert either the needle 10 itself, as shown in FIGS. 6c and 6d, or a needle gripper, as shown in the previous drawings of this application.

Figure 7:
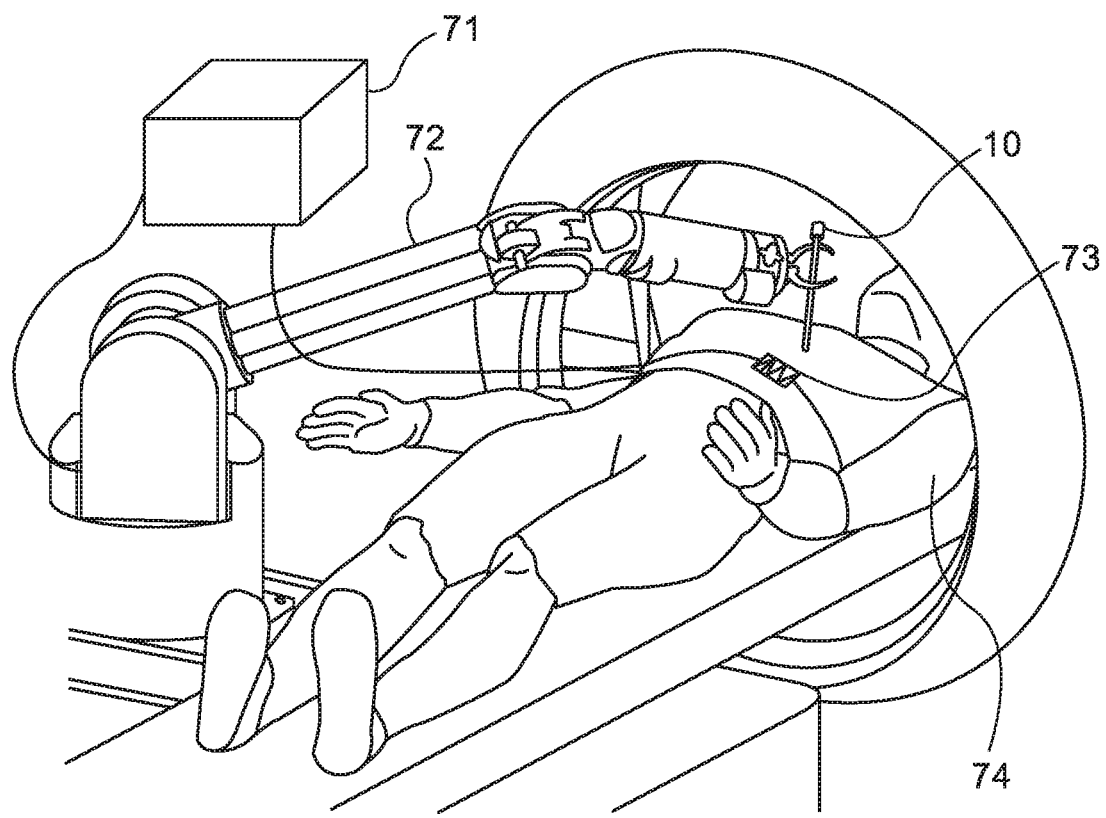
FIG. 7 illustrates a complete robotic needle insertion system, actuated on a subject being imaged in a CT system.

Reference is now made to FIG. 7, which illustrates a complete robotic needle insertion system, showing some of the overall features enabled by the use of the devices of the present disclosure. In FIG. 7 there is shown a subject 74 being imaged in a CT system. In this exemplary system, the robot 72 used for the insertion of the needle 10 is a serial robot, mounted by the CT-bedside. However, it is to be understood that any suitable robot for needle insertion can equally well be used, and especially the type of miniature robots shown in the current applicant's co-pending PCT Patent Application for "Needle Steering by Shaft Manipulation". Though only schematically shown in FIG. 7, the needle 10 is held by the robot arm in a releasable gripper device, such as any of the types whose operational model are described in this disclosure. A motion or respiration sensor 73 is mounted on the body of the subject to provide data regarding the breathing cycle of the subject. The data from this sensor is input to the system controller 71, where it is used to synchronize at least one of the needle insertion and the needle gripping and release action with a point of time in the breathing cycle.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

The invention claimed is:

1. A system for inserting a medical tool into a subject, the system comprising:
   a capture unit configured for alternately and repeatedly gripping and releasing either of the medical tool or a holder configured for holding the medical tool;
   a controllable drive mechanism configured for inserting the medical tool into the subject in a series of insertion steps, the controllable drive mechanism being further configured for synchronizing with the capture unit to enable gripping of the medical tool or the holder during an insertion step and partial releasing of the medical tool or the holder between insertion steps which leaves a partial limiting linkage with the capture unit, allowing the medical tool free movement with one or more limited degrees of freedom; and
   a tracking system configured for determining the relative position between the medical tool or the holder and the capture unit;
   wherein the system is configured for moving the capture unit toward the medical tool or the holder based on the relative position determined by the tracking system.

2. The system according to claim 1, further comprising a breathing monitoring system configured for monitoring the breathing of the subject.

3. The system according to claim 2, wherein the breathing monitoring system comprises at least one breathing tracking sensor.

4. The system according to claim 2, wherein the system is configured to synchronize the releasing and the gripping of the medical tool or the holder with the breathing cycle of the subject, such that said capture unit can be commanded to grip the medical tool or the holder at a predetermined point in time of the subject's breathing cycle.

5. The system according to claim 1, wherein the controllable drive mechanism is either a robotic actuator attached to the capture unit or a motion mechanism configured for moving the medical tool or the holder relative to the capture unit.

6. The system according to claim 1, wherein the tracking system comprises at least one emitter and at least one sensor, and wherein one of the at least one emitter and the at least one sensor is disposed on the medical tool or the holder, and the other of the at least one emitter and the at least one sensor is disposed on the capture unit.

7. The system according to claim 4, comprising a tracking sensor configured to determine the position of the body of said subject close to the point of insertion of said medical tool.

8. The system according to claim 5, wherein said at least one tracking sensor is part of an external tracking system.

9. The system according to claim 1, wherein:
   the holder comprises a protrusion;
   the capture unit comprises mechanical clamping jaws; and the system further comprises an actuation mechanism configured for closing the clamping jaws on the protrusion, wherein when the medical tool or a holder is released, it is constrained by the mechanical clamping jaws which constrain the medical tool position to within its confines.

10. The system according to claim 1, wherein:

the holder comprises a first set of locating features and a locating spigot;

the capture unit comprises a second set of locating features configured for mating with the first set of locating features on the holder, and a clamping system configured for closing on the locating spigot; and the system further comprises an actuating mechanism configured for closing the clamping system on the locating spigot after the first and second sets of locating features are mated.

11. The system according to claim 1, wherein:

the holder comprises a first set of locating features and a ferromagnetic section;

the capture unit comprises a second set of locating features configured for mating with the first set of locating features on the holder, and a source of magnetic field; and the system further comprises an actuation mechanism configured for activating the source of magnetic field.

12. A system for inserting a medical tool into a subject, the system comprising:

a controllable drive mechanism configured for inserting the medical tool into the subject in a series of insertion steps;

a capture unit configured for alternately and repeatedly gripping and releasing either of the medical tool or a holder configured for holding the medical tool; and a tracking system configured for determining the position of the medical tool or the holder relative to the capture unit;

wherein the controllable drive mechanism is configured to be synchronized with the capture unit to enable gripping of the medical tool or the holder by the capture unit during an insertion step and partial releasing of the medical tool or the holder from the capture unit between insertion steps which leaves a partial limiting linkage with the capture unit, allowing the medical tool free movement with one or more limited degrees of freedom, and wherein the system is configured to correlate the position of the capture unit to the position of the medical tool or the holder, using the tracking system, and to position the controllable drive mechanism such that each gripping action is executed at essentially the same position in space as the respective position of release of the medical tool or the holder following the previous insertion step.

13. The system according to claim 12, further comprising a breathing monitoring system configured for monitoring the breathing cycle of the subject.

14. The system according to claim 13, wherein the breathing monitoring system comprises at least one breathing tracking sensor.

15. The system according to claim 13, wherein the system is configured to synchronize the insertion steps with the breathing cycle of the subject, such that the insertion steps and the releasing and gripping of the medical tool or the holder are performed in substantially the same part of each breathing cycle of the subject.

16. A method for controllably inserting a medical tool into a subject, the method comprising:

inserting the medical tool into the subject in a series of insertion steps;

activating a capture unit to grip either of the medical tool or a holder configured to hold the medical tool during an insertion step;

activating the capture unit to partial releasing the medical tool or the holder between insertion steps;

tracking the position of the medical tool or the holder relative to the capture unit using a tracking system;

monitoring the subject's breathing cycle using a tracking sensor, and synchronizing the gripping of said medical tool or the holder with the subject's breathing cycle, such that the insertion steps are performed in substantially the same part of each breathing cycle of the subject.

17. The method according to claim 16, further comprising the step of synchronizing the partial releasing of the medical tool or the holder with the subject's breathing cycle.

* * * * *